United States Patent [19]

Ikarashi et al.

[11] Patent Number: 4,990,651
[45] Date of Patent: Feb. 5, 1991

[54] PROCESS FOR PRODUCING CARBOXYLIC ACID ESTERS

[75] Inventors: Hideo Ikarashi; Yoshio Kawai; Seiji Nagasawa; Hiroyuki Hirayama, all of Niigata, Japan

[73] Assignee: Mitsubishi Gas Chemical Company, Inc., Tokyo, Japan

[21] Appl. No.: 336,730

[22] Filed: Apr. 12, 1989

[30] Foreign Application Priority Data

May 16, 1988 [JP] Japan .................. 63-116970

[51] Int. Cl.$^5$ .............................. C07C 69/76
[52] U.S. Cl. .................... 560/103; 546/319; 560/38; 560/60; 560/106; 560/155; 560/173; 560/179; 560/188; 560/205; 560/215; 560/265; 564/137
[58] Field of Search .................. 560/38, 60, 103, 179, 560/215, 234, 265, 106, 155, 173, 188, 205; 564/137; 546/319

[56] References Cited

U.S. PATENT DOCUMENTS

| | | | |
|---|---|---|---|
| 4,055,590 | 10/1977 | Gruber | 560/179 |
| 4,613,684 | 9/1986 | Aoyama | 560/179 |

FOREIGN PATENT DOCUMENTS

| | | |
|---|---|---|
| 52-3015 | 1/1977 | Japan . |
| 53-141216 | 12/1978 | Japan . |
| 53-144524 | 12/1978 | Japan . |
| 57-67534 | 4/1982 | Japan . |
| 58-49338 | 3/1983 | Japan . |
| 58-55444 | 4/1983 | Japan . |
| 60-78937 | 5/1985 | Japan . |

*Primary Examiner*—Michael L. Shippen
*Attorney, Agent, or Firm*—Frishauf, Holtz, Goodman & Woodward

[57] ABSTRACT

Carboxylic acid esters, industrially important compounds, are obtained by reacting carboxylic acid amides and formic acid esters, or carboxylic acid amides, alcohols and carbon monoxide in the presence of metal alcoholate.

10 Claims, No Drawings

PROCESS FOR PRODUCING CARBOXYLIC ACID ESTERS

BACKGROUND OF THE INVENTION

1. Field of the Invention

The present invention relates to a process for efficiently producing carboxylic acid esters from carboxylic acid amides and formic acid esters or alternatively from carboxylic acid amides, alcohols and carbon monoxide.

2. Description of Related Arts

Carboxylic acid esters are industrially important compounds. These carboxylic acid esters can be produced from carboxylic acid amides: for example, methyl acetate is produced from acetic acid amide; methyl methacrylate from methacrylic acid amide; methyl acrylate from acrylic acid amide; or methyl α-hydroxyisobutyrate from α-hydroxyisobutyric acid amide. For producing carboxylic acid esters from carboxylic acid amides, a method of reacting carboxylic acid amides with alcohols in the presence of sulfuric acid is well known. This method is widely employed for industrial production of methyl methacrylate.

This method, however, has disadvantages in that a large amount of acidic ammonium sulfate results as a by-product, leading to a marked increase in production costs owing to its disposal, and expensive corrosion-resistant apparatus is also required.

In order to overcome the above problems, a method of producing carboxylic acid esters by reacting carboxylic acid amides with alcohols without the use of sulfuric acid has been proposed. In Japanese Patent Application Laid-Open Nos. 3015/1977, 141216/1978 and 144524/1978, for example, the reaction is carried out in a liquid phase in the presence of e.g. metal salts or metal alcoholates. On the other hand, in Japanese Patent Application Laid-Open Nos. 67534/1982 and 49338/1983, the reaction is carried out in a gas phase in the presence of a solid acid catalyst.

These methods, however, have disadvantages in that the yield of the desired carboxylic acid ester or its selectivity is low and thus are not satisfactory for commercial practice thereof. Moreover, in commercial practice, they suffer from problems in that: (1) the reaction should be carried out at high temperatures, (2) in case of the liquid phase reaction, high pressure is needed, (3) a large amount of ammonia is produced during the reaction and thus its recovery and separation is needed, and (4) the reaction of the ammonia with carboxylic acids as by-product leads to the formation of ammonium salts thereof.

A method of producing carboxylic acid esters and formamide by reacting carboxylic acid amides with formic acid esters, or alcohols and carbon monoxide has been developed, as described in Japanese Patent Application Laid-Open Nos. 55444/1983 and 78937/1985.

In Japanese Patent Application Laid-Open No. 55444/1983, main catalysts comprising metal salts of organic or inorganic acids, or metal chelate compounds, and an accelerator comprising nitrogen or phosphorus-containing organic compounds are used in combination. In one of the examples, the reaction was carried out at 185 to 250° C. for 2 to 4.5 hours, and the desired carboxylic acid ester was obtained in a yield of 16.3 to 78.9%. This yield, however, cannot be said to be sufficiently high, and moreover the catalyst system is expensive.

In Japanese Patent Application Laid-Open No. 78937/1985, a catalyst system consisting of the combination of amidine or tertiary amine and metal carbonyl is used, and the reaction is carried out under pressure of carbon monoxide. However, although the selectivity of the carboxylic acid ester is relatively high, this method has disadvantages in that high pressure is needed for the reaction, highly toxic metal carbonyl is used, and the catalyst system is expensive.

SUMMARY OF THE INVENTION

An object of the present invention is to provide an improved process for producing carboxylic acid esters from carboxylic acid amides and formic acid esters, or carboxylic acid amides, alcohols and carbon monoxide.

Another object of the present invention is to provide an improved process for producing both carboxylic acid esters and formamide from starting materials as described above.

It has been found that if metal alcoholate is used as a catalyst, the reaction proceeds efficiently under much milder conditions than in the conventional methods and the desired carboxylic acid esters and formamide can be obtained in a high selectivity.

The present invention relates to a process for producing carboxylic acid ester which comprises reacting carboxylic acid amides and formic acid esters, or alternatively reacting carboxylic acid amides, alcohols and carbon monoxide, in the presence of metal alcoholates.

DESCRIPTION OF PREFERRED EMBODIMENTS

Carboxylic acid amides to be used in the present invention include aliphatic or aromatic carboxylic acid amides, and α-hydroxy or α-aminocarboxylic acid amides. These amides can be prepared by hydrolyzing nitriles, or by reacting amines with carbon monoxide, for example. Specific examples are acetamide, lactic acid amide, acrylic acid amide, methacrylic acid amide, α-hydroxyisobutyric acid amide, benzamide, valine amide and alanineamide.

Formic acid esters to be used in the present invention are those prepared from formic acid, and aliphatic alcohols having 1 to 10 carbon atoms or alicyclic alcohols having 4 to 10 carbon atoms. Specific examples of the aliphatic alcohols are methanol, ethanol, propanol, butanol and octanol. Specific examples of the alicyclic alcohols are cyclohexanol and cycloheptanol.

In the process of the present invention, a combination of alcohols and carbon monoxide can be used instead of formic acid esters. Alcohols to be used herein are the same as those constituting formic acid esters described above.

Metal alcoholates (metal alkoxides) to be used in the present invention are prepared from alkali metals, e.g. lithium, sodium or potassium, or alkali earth metals, e.g. magnesium, calcium or barium, and lower aliphatic alcohols. Specific examples are sodium methylate, sodium ethylate, sodium butyrate, potassium methylate, lithium butylate, magnesium methylate, calcium methylate or barium methylate.

The amount of the metal alcoholate used in the present invention is preferably 0.001 to 0.3 mol, and more preferably 0.003 to 0.2 mol per mol of the carboxylic acid amide.

The reaction of the present invention is an equilibrium reaction, and the conversion greatly varies with the molar ratio of carboxylic acid amide to formic acid ester, or to alcohols and carbon monoxide. From an industrial production viewpoint of carboxylic acid ester, the amount of the formic acid ester is preferably 1 to 10 mol per mol of the carboxylic acid amide.

When alcohols and carbon monoxide are used in place of the formic acid ester, the amount of the alcohols and carbon monoxide is preferably 1 to 10 mol per mol of the carboxylic acid amide, respectively.

Carboxylic acid amides are generally in solid state at ordinary temperature, and thus a suitable solvent is preferably used in the present invention. When formic acid ester is used as the starting material, an alcohol constituting it is preferably used for a solvent. On the other hand, when alcohol and carbon monoxide are used as the starting materials, it is preferred that the alcohol be used in an excessive amount so as to act as a solvent for the carboxylic acid amide.

The reaction temperature and period of time can be chosen from a wide range depending on the kind of the starting material, the amount of the catalyst charged, and the conversion objective. In general, the reaction temperature is preferably 0 to 200° C. and more preferably 20 to 150° C., and the reaction period of time is preferably 0.2 to 24 hours and more preferably 0.5 to 10 hours.

The present invention is described in greater detail with reference to the following examples, although it is not intended to be limited thereto.

EXAMPLE 1

10.3 g (0.1 mol) of α-hydroxyisobutyric acid amide, 32 g (1.0 mol) of methanol and 4.4 g (0.08 mol) of sodium methylate were placed in a 120-milliliter stainless steel autoclave, and the atmosphere in the autoclave was replaced with carbon monoxide. Then pressured carbon monoxide was introduced and the contents were agitated while heating under pressure of carbon monoxide.

When the temperature in the autoclave reached 80° C., the reaction pressure was raised to 40 kg/cm$^2$, and the reaction was continued for 3 hours while introducing carbon monoxide. After completion of the reaction, the reaction mixture was cooled to 10° C. and the pressure was returned to atmospheric pressure. Then the contents were taken out of the autoclave and subjected to a gas chromatographic analysis. This analysis showed that the conversion of α-hydroxyisobutyric acid amide was 65%, the selectivity into methyl α-hydroxyisobutyrate was 95.2%, and the selectivity into formamide (based on α-hydroxyisobutyric acid amide) was 92.8%.

EXAMPLE 2

The procedure of Example 1 was repeated with the exception that 18 g (0.3 mol) of methyl formate and 9.6 g (0.3 mol) of methanol were reacted without the use of carbon monoxide, and the reaction temperature was changed to 30° C.

The conversion of α-hydroxyisobutyric acid amide was 70%, the selectivity into methyl α-hydroxyisobutyrate was 98.8%, and the selectivity into formamide (based on α-hydroxyisobutyric acid amide) was 97.5%.

EXAMPLE 3

The procedure of Example 1 was repeated with the exception that 5.9 g (0.1 mol) of acetic acid amide was used as the carboxylic acid amide.

The conversion of acetic acid amide was 58.5%, the selectivity into methyl acetate was 97.5%, and the selectivity into formamide was 94.8%.

EXAMPLE 4

The procedure of Example 1 was repeated with the exception that 8.5 g (0.1 mol) of methacrylic acid amide was used as the carboxylic acid amide.

The conversion of methacrylic acid amide was 68.5%, the selectivity into methyl methacrylate was 93.8%, and the selectivity into formamide was 93.2%.

EXAMPLE 5

The procedure of Example 1 was repeated with the exception that 11.6 g (0.1 mol) of valine amide was used as the carboxylic acid amide.

The conversion of valine amide was 72%, the selectivity into methyl ester of valine was 92.4%, and the selectivity into formamide was 93.5%.

EXAMPLE 6

The procedure of Example 1 was repeated with the exception that 12.2 g (0.1 mol) of nicotinic acid amide was used as the carboxylic acid amide.

The conversion of nicotinic acid amide was 64.8%, the selectivity into methyl nicotinate was 91.9%, and the selectivity into formamide was 92.8%.

EXAMPLE 7

The procedure of Example 1 was repeated with the exception that 74.0 g (1.0 mol) of butanol was used as the alcohol.

The conversion of α-hydroxyisobutyric acid amide was 75.5%, the selectivity into butyl α-hydroxyisobutyrate was 94.7%, and the selectivity into formamide was 92.2%.

EXAMPLE 8

The procedure of Example 1 was repeated with the exception the amount of sodium methylate was changed to 0.77 g (0.015 mol), and the reaction was carried out at a temperature of 60° C. for 5 hours.

The conversion of α-hydroxyisobutyric acid amide was 58.6%, the selectivity into methyl α-hydroxyisobutyrate was 92.6%, and the selectivity into formamide was 84.9%.

EXAMPLE 9

The procedure of Example 1 was repeated with the exception that 1.05 g (0.015 mol) of potassium methylate was used in place of the sodium methylate.

The conversion of α-hydroxyisobutyric acid amide was 62.4%, the selectivity into methyl α-hydroxyisobutyrate was 93.5%, and the selectivity into formamide was 94.2%.

EXAMPLE 10

The procedure of Example 1 was repeated with the exception that 1.53 g (0.015 mol) of calcium methylate was used in place of the sodium methylate.

The conversion of α-hydroxyisobutyric acid amide was 60.5%, the selectivity into methyl α-hydroxyisobutyrate was 92.8%, and the selectivity into formamide was 90.5%.

EXAMPLE 11

The procedure of Example 1 was repeated with the exception that 1.29 g (0.015 mol) of magnesium methylate was used in place of the sodium methylate.

The conversion of α-hydroxyisobutyric acid amide was 64.2%, the selectivity into methyl α-hydroxyisobutyrate was 96.8%, and the selectivity into formamide was 95.7%.

What is claimed is:

1. In a process for producing carboxylic acid ester which comprises reacting, in the presence of a catalyst, carboxylic acid amide and formic acid ester, or carboxylic acid amide, alcohol and carbon monoxide, the improvement wherein the catalyst is an alkali metal alcoholate or alkaline earth metal alcoholate.

2. The process as claimed in claim 1, wherein the metal alcoholate is at least one compound selected from the group consisting of sodium methylate, sodium ethylate, sodium butyrate, potassium methylate, lithium butyrate, magnesium methylate, calcium methylate and barium methylate.

3. The process as claimed in claim 1, wherein the amount of the metal alcoholate is 0.001 to 0.3 mol per mol of the carboxylic acid amide.

4. The process as claimed in claim 1, wherein the carboxylic acid amide is aliphatic carboxylic acid amide, aromatic carboxylic acid amide, aliphatic α-hydroxyl carboxylic acid amide, aromatic α-hydroxylcarboxylic acid amide, aliphatic α-aminocarboxylic acid amide or aromatic α-aminocarboxylic acid amide.

5. The process as claimed in claim 1, wherein the carboxylic acid amide is at least one compound selected from the group consisting of acetamide, lactic acid amide, acrylic acid amide, methacrylic acid amide, α-hydroxyisobutyric acid amide, benzamide, valine amide and alanineamide.

6. The process as claimed in claim 1, wherein the formic acid ester is at least one compound prepared by reacting formic acid with aliphatic alcohols having 1 to 10 carbon atoms or alicyclic alcohols having 4 to 10 carbon atoms.

7. The process as claimed in claim 1, wherein the amount of the formic acid ester is 1 to 10 moles per mol of the carboxylic acid amide.

8. The process as claimed in claim 1, wherein the alcohol is at least one compound selected from the group consisting of methanol, ethanol, propanol, butanol, octanol, cyclohexanol and cycloheptanol.

9. The process as claimed in claim 2, wherein the amount of the metal alcoholate is 0.001 to 0.3 mol per mol of the carboxylic acid amide.

10. The process as claimed in claim 9, wherein the carboxylic acid amide is aliphatic carboxylic acid amide, aromatic carboxylic acid amide, aliphatic α-hydroxyl carboxylic acid amide, aromatic α-hydroxylcarboxylic acid amide, aliphatic α-aminocarboxylic acid amide or aromatic α-aminocarboxylic acid amide;

the carboxylic acid amide is at least one compound selected from the group consisting of acetamide, lactic acid amide, acrylic acid amine, methacrylic acid amide, α-hydroxyisobutyric acid amide, benzamide, valine amide and alanineamide;

the formic acid ester is at least one compound prepared by reacting formic acid with aliphatic alcohols having 1 to 10 carbon atoms or alicyclic alcohols having 4 to 10 carbon atoms and the amount of the formic acid ester is 1 to 10 moles per mol of the carboxylic acid amide; and the alcohol is at least one compound selected from the group consisting of methanol, ethanol, propanol, butanol, octanol, cyclohexanol and cycloheptanol.

* * * * *